United States Patent [19]

Day et al.

[11] Patent Number: 5,011,677
[45] Date of Patent: Apr. 30, 1991

[54] RADIOACTIVE GLASS MICROSPHERES

[75] Inventors: Delbert E. Day, Rolla; Gary J. Ehrhardt, Columbia, both of Mo.

[73] Assignee: The Curators of the University of Missouri, Columbia, Mo.

[21] Appl. No.: 234,017

[22] Filed: Aug. 18, 1988

Related U.S. Application Data

[62] Division of Ser. No. 673,123, Nov. 19, 1984, Pat. No. 4,789,501.

[51] Int. Cl.$^5$ ............... A61K 43/00; A61N 5/00; C03C 12/00
[52] U.S. Cl. .................... 424/1.1; 252/645; 128/654; 501/33; 600/3
[58] Field of Search .............. 424/1.1; 252/645; 600/3; 128/654; 501/33

[56] References Cited

U.S. PATENT DOCUMENTS

| | | | |
|---|---|---|---|
| 3,334,050 | 8/1967 | Grotenhuis et al. | 252/301.1 |
| 4,350,675 | 9/1982 | Drake | 424/1.1 |
| 4,403,615 | 9/1983 | Hoehner | 128/692 |
| 4,745,907 | 5/1988 | Russel, Jr. et al. | 128/654 X |

OTHER PUBLICATIONS

Grady, et al., "Intra-arterial Radioisotopes to Treat Cancer", American Surgeon, vol. 26, pp. 678–684, 1960.
Makishima, et al., "Elastic Moduli and Refractive Indices of Aluminosilicate Glasses Containing $Y_2O_3$, $La_2I_3$, and $TiO_2$", Journal of the American Ceramic Society, vol. 61, pp. 247–249, May–Jun. 1978.
Loeehman, "Preparation and Properties of Yttrium–Silicon–Aluminum Oxynitride Glasses", Journal of the American Ceramic Soc. vol. 62, pp. 491–494, Sep.–Oct. 79.
Makishima, et al., "Alkaline Durability of High Elastic Modulus Alumino-Silicate Glasses Containing $Y_2O_3$, $La_2O_3$ & $TiO_2$", Journal of Non-Crystalline Solids 38 & 39, pp. 661–666, 1980.
Bonder, et al., "Phase Equilibria in the System $Y_2O_3$–$Al_2O_3$–$SiO_2$", I. V. Grebenschikov Institute of Silicate Chemistry, Academy of Sciences, USSR, translated from Izvestiya Akademii Nauk SSSR, Seriya Khimicheskaya, No. 7, pp. 1325–1326, Jul. 1964.
Sedykh, et al., "Refractive Indices in the System $Y_2O_3$–$SiO_2$–$Al_2O_3$ in the Vitrification Region", State Scientific-Research and Design Instute of the Rare Metals Industry, translated from Izvestiya Akademii Nauk SSSR, Neorganicheskie Materialy, vol. 11, No. 6, pp. 1153–1154, Jun. 1975.
Antonova, et al., "Thermal Endurance of Glass Based on $Y_2O_3$–$Al_2O_3$–$SiO_2$", Izv. Akad. Nauk SSR, Neorg. Mater. 12(4): 783–784, 1976.

Primary Examiner—John S. Maples
Attorney, Agent, or Firm—Senniger, Powers, Leavitt & Roedel

[57] ABSTRACT

A radioactive microsphere for radiation therapy of a mammal comprising a biologically compatible glass material containing a beta or gamma emitting radioisotope distributed substantially uniformly throughout the glass. Advantageously, the radioisotope is produced by irradiation of the microsphere.

45 Claims, 5 Drawing Sheets

RADIOACTIVE GLASS MICROSPHERES

This is a division of application Ser. No. 623,123, filed Nov. 19, 1984, now U.S. Pat. No. 4,789,501.

BACKGROUND OF THE INVENTION

The present invention relates generally to microspheres useful in the treatment of cancerous and tumor bearing tissue and more particularly to novel glass microspheres useful in this treatment.

In the treatment of patients with certain kinds of cancer, methods are known in which radioactive particles are introduced intravascularly in order to trap the radioactive particle at a particular site for its radiation effect. According to this technique, a small quantity of the radioactive particles are injected into the patient and a diffuse, homogeneous field of radiation within a selected region of the body is achieved by permanent lodgement of the particles in the capillary bed of the proposed area, typically the location of a tumor. In early applications of this technique, yttrium oxide powder was suspended in a viscous medium prior to administration. Yttrium was selected for the technique because of its suitable characteristics: it emits nearly 100 percent beta radiation. See, e.g., Nolan, et al., "Intravascular Particulate Radioisotope Therapy", *The American Surgeon* 35: 181-188 (1969) and Grady, et. al., "Intra-Arterial Radioisotopes to Treat Cancer", *American Surgeon* 26 678-684 (1960). This method is not totally satisfactory, however. Two disadvantages of yttrium oxide powder are its high density (5.01 gm/cm$^3$) and irregular particle shape. The high density of pure yttrium oxide powder makes it difficult to keep the particles in suspension in the liquids used to inject them into the body, and accelerates their tendency to settle in the blood stream prior to reaching the desired tumor. The sharp corners and edges of yttrium oxide particles also irritate surrounding tissue in localized areas, and interfere with the uniform distribution of the radioactive particles in the tumor to be treated.

In later applications, the particles used have been microspheres composed of an ion exchange resin, or crystalline ceramic core, coated with a radioactive isotope such as P-32 or Y-90. Both ion exchange resin and crystalline ceramic microspheres offer the advantage of having a density much lower than that of yttrium oxide particles, and the ion exchange resin offers the additional advantage of being particularly easy to label. See, e.g., Zielinski and Kasprzyk, "Synthesis and Quality Control Testing of 32P labelled Ion Exchange Resin Microspheres for Radiation Therapy of Hepatic Neoplasms", *Int. J. Appl. Radiat. Isot.* 34: 1343-1350 (1983). However, whenever a microsphere comprises a core material having an external surface coating which contains the radioactive isotope there is a risk that the radioactive coating may separate from the underlying microsphere core. Any mechanical breakage of the coating can release unwanted radioactivity to other parts of the human body which is highly undesirable. Further disadvantages are presented by the special handling and precautions that are necessary to coat a radioactive isotope onto a crystalline ceramic core, or to label ion exchange resin.

In still another application, microspheres have been prepared comprising a ceramic material and having a radioactive isotope incorporated into the ceramic material. While the release of radioactive isotopes from a radioactive coating into other parts of the human body may be eliminated by incorporating the radioisotopes into ceramic spheres, the latter product form is nevertheless not without its disadvantages. Processing of these ceramic microspheres is complicated because potentially volatile radioactivity must be added to ceramic melts and the microspheres must be produced and sized while radioactive, with concomitant hazards of exposure to personnel and danger of radioactive contamination of facilities.

Consequently, a need has remained for a microsphere which is useful in the treatment of cancer or tumor bearing tissue, but which will not release a radioactive coating or isotope into remote parts of the body of the patient after administration, will not require any technicians to handle any radioactive materials during the formation and spheroidization of the microsphere and which have a density which will permit the microspheres to be suspended in a fluid suitable for injection into a human.

SUMMARY OF THE INVENTION

Among the several objects of the invention, therefore may be noted the provision of a novel microsphere for use in radiation therapy; the provision of such a microsphere wherein the radioactive isotope is uniformly distributed throughout the microsphere material; the provision of such a microsphere wherein there is no significant release of the radioactive isotope from the microsphere into the body of the patient; the provision of such a microsphere in which the microsphere is completely nonradioactive until irradiated for use in therapy; the provision of such a microsphere which contains a stable element or isotope that can be activated to a beta or gamma radiation emitting isotope by neutron irradiation; the provision of such a microsphere which contains a number of stable elements or isotopes that which forms a number of beta or gamma radiation emitting isotopes simultaneously during neutron activation, thereby permitting wide variation in the rate at which the radiation is delivered to the body; the provision of such a microsphere wherein the density of the sphere is substantially less than that of yttrium oxide particles; the provision of formulations for treatment of tumors by parenteral administration; and the provision of processes for radiation therapy as well as the manufacture of microspheres of the present invention.

Briefly, therefore, the present invention is directed to novel radioactive microspheres which may be used for radiation therapy of a mammal. These radioactive microspheres comprise a biologically compatible glass material containing a beta or gamma radiation emitting radioisotope distributed substantially uniformly throughout the glass.

In another aspect, the present invention is directed to radioactive microspheres adapted for radiation therapy of a mammal. These radioactive microspheres comprise a biologically compatible glass material containing a beta or gamma radiation emitting radioisotope distributed substantially uniformly throughout the glass. The microsphere is substantially spherical in shape and has a diameter in the range of about 5 to about 75 micrometers.

Another aspect of the present invention is directed to radioactive microspheres adapted for radiation therapy of a mammal. These radioactive microspheres comprise a biologically compatible glass material having a radioisotope emitting a therapeutic amount of beta or gamma radiation and a balance of elements which either do not become radioactive during neutron irradiation or which have a half-life that is sufficiently short so that the element does not emit a significant amount of beta or gamma radiation at the time of administration.

A further aspect of the present invention is directed to novel microspheres adapted for radiation therapy of a mammal. These microspheres comprise a biologically compatible glass having an isotope distributed substantially uniformly throughout the glass. These microspheres are substantially spherical in shape and the isotope is selected from the group consisting of phosphorus-32 and yttrium-90 and stable isotopes which are activatable by neutron irradiation to produce phosphous-32 or yttrium-90.

A further aspect of the present invention is directed to novel glass microspheres adapted for radiation therapy of a mammal. These glass microspheres comprise silica, alumina and yttria and have a diameter of less than about 75 micrometers.

A still further aspect of the present invention is directed to a method of preparing a microsphere for use in a radiation therapy procedure. The method comprises irradiating a microsphere comprising a glass material containing a stable element or isotope and thereby activating the element or isotope to a beta or gamma radiation emitting isotope.

A still further aspect of the present invention is directed to a method of radiation therapy for a mammal. This method comprises administering to the mammal, glass microspheres containing a beta or gamma radiation emitting radioisotope distributed substantially uniformly throughout the glass.

A further aspect of the present invention is directed to novel microspheres adapted for irradiation and subsequent use in radiation therapy of a mammal. The microspheres comprise a glass material containing phosphorus or yttrium distributed substantially uniformly throughout the glass and a balance of elements selected from the group consisting of those elements which either do not become radioactive during neutron irradiation or which have a half-life that is sufficiently short so that the element does not emit a significant amount of beta or gamma radiation at the time of administration.

A further aspect of the present invention is directed to novel microspheres adapted for radiation therapy of a mammal. These microspheres comprise a glass material containing an element distributed substantially uniformly throughout the glass and which, upon being subjected to an effective amount of neutron irradiation, emits a therapeutic intensity and amount of beta or gamma radiation. The balance of elements contained by the microsphere are selected from the group consisting of carbon, nitrogen, oxygen, fluorine, sodium, magnesium, aluminum, silicon, potassium, vanadium, manganese, gallium, niobium, iodine, lead, titanium, copper, germanium, and zirconium.

A still further aspect of the present invention is directed to a radioactive glass material adapted for radiation therapy of a mammal. The glass material comprises an yttrium oxide-aluminosilicate glass having a composition lying substantially within a quadrilateral region of the ternary composition diagram of the yttria-alumina-silica system. This quadrilateral region of the ternary diagram is defined by its four corners having the following combination of weight proportions of the components: 20% silica, 10% alumina, 70% yttria; 70% silica, 10% alumina, 20% yttria; 70% silica, 20% alumina, 10% yttria; and 20% silica, 45% alumina, 35% yttria.

A still further aspect of the present invention is directed to a glass material adapted for radiation therapy of a mammal. The glass material comprises between about 50 and about 70 wt. % silica, between about 1 and about 17 wt. % alumina; between about 5 and about 9 wt. % magnesia; and between about 2 and about 10 wt. % phosphorus pentoxide.

DESCRIPTION OF THE PREFERRED EMBODIMENT

In accordance with the present invention, novel microspheres have been devised for use in the therapy of certain cancers and tumor bearing tissue. These novel microspheres comprise a glass material having a stable element which can be activated by neutron irradiation to produce a beta or gamma radiation emitting isotope distributed substantially uniformly throughout the glass. Thus, these novel microspheres may be manufactured and sized before radioactivity is induced, thereby avoiding the necessity of either adsorbing a radioelement onto the microsphere surface, or adding radioelements to a high temperature melt and spheroidizing and sizing the particles while intensely radioactive.

Various biologically compatible glasses may be used in preparing the microspheres of the present invention. Preferably, these glasses are good solvents for small amounts of nearly all oxides and have sufficient chemical durability so that, after the microspheres are administered to a target portion of the patient's body, no significant amount of any radioactive isotope is lost from the patient's body or transformed to other parts of the patient's system. It is further preferred that the glasses do not incorporate any elements that may cause the microsphere to emit any significant amount of undesired radiation. In accordance with a preferred embodiment of the present invention, many aluminosilicate glasses and lead silicate glasses have been found to be good solvents for small amounts of nearly all oxides, thereby permitting great versatility: the dose and profile of the radiation emitted by microsphere may be controlled by incorporating elements having the desired emission characteristics after irradiation. Many aluminosilicate and lead silicate glasses also have sufficient chemical durability to prevent the loss of a significant amount of the radioactive isotope into the patient's system after the microsphere is administered, yet do not need to contain any elements that may cause the microsphere to emit a significant amount of undesired radiation. Various aluminosilicate glasses and lead silicate glasses thus may be used in accordance with a preferred embodiment of the present invention. For instance, preferred glasses incorporating yttrium are yttrium oxide-aluminosilicate (YAS) glass compositions lying substantially within a quadrilateral region of the ternary composition diagram of the yttria-alumina-silica system, the quadrilateral region being defined by the four corners having the following specified weight proportions of each of the components:

| $SiO_2$ | $Al_2O_3$ | $Y_2O_3$ |
|---|---|---|
| 20% | 10% | 70% |
| 70% | 10% | 20% |
| 70% | 20% | 10% |
| 20% | 45% | 35% |

Figure 1:
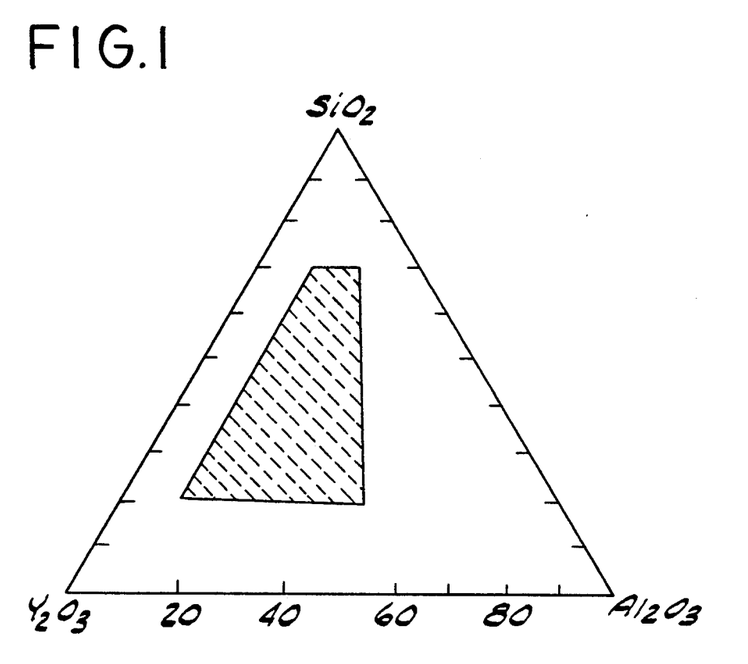
FIG. 1 is a ternary composition diagram of the yttria-alumina-silica system with a cross-hatched region designating preferred glasses for use in the microspheres of the present invention.

This quadrilateral region is shown in FIG. 1. The density of the YAS glasses is preferably within the range of about 2.7 to about 3.9 grams/cc. By way of further example, preferred glasses incorporating phosphorus comprise silica, alumina, magnesia and phosphorus containing between about 50 and about 70 wt. % silica, between about 1 and about 17 wt. % alumina, between about 5 and about 9 wt. % magnesia and between about 2 and about 10 wt. % phosphorus pentoxide. The density of the glasses incorporating phosphorus is preferably within the range of about 2.2 to about 2.7 grams/cc.

The microspheres of the present invention may comprise essentially void-free glass microspheres, microshells, i.e., microspheres having a hollow core or glass microspheres having a "foam-like" structure where the microsphere has a plurality of hollow cells. Microshells and microspheres having a plurality of hollow cells may be preferred where it is desired to employ a microsphere having a density substantially less than that of the essentially void-free microsphere.

Whether the microspheres of the present invention are essentially void-free, microshells, or have a plurality of hollow cells, it is preferred that the microspheres be substantially spherical, i e., there are no sharp edges or points that would cause the microsphere to lodge in a location other than that desired. In this context, elipsoidal and other similarly shaped particles that do not have sharp edges or points would be considered to be substantially spherical in shape.

In a preferred embodiment of the present invention, the constituent elements of the microspheres are chosen so that when administered to the patient, the microspheres emit a therapeutic intensity and amount of short-range (e.g., a penetration of the tissue on the order of about several millimeters or less) beta or gamma radiation but will not emit a significant amount of unwanted beta or gamma radiation which could have a negative impact on healthy tissue surrounding the cancerous or tumor bearing tissue. In this regard, it is preferred that the constituent elements of the glass be selected so that the therapeutic radiation emitting radioisotopes are the only constituent isotopes which may emit a significant amount of radiation beyond a relatively short period of time, e.g., on the order of about 1 week or less. Elements such as yttrium and phosphorus which form radioisotopes having a half-life greater than about two days and less than about 30 days are particularly preferred as the elements which emit therapeutic radiation. The balance of the constituent elements of the glass are preferably selected so that when administered, the microsphere does not emit any significant amount of radiation other than that emitted by Y-90 or P-32. This result may be accomplished by selecting a glass composition that contains yttrium-89 or phosphorus-31 and a balance of elements which either do not become radioactive during neutron irradiation or which have a sufficiently short half-life so as not to emit a significant amount of beta or gamma radiation at the time of administration. Elements which either do not become radioactive during neutron irradiation or which have a sufficiently short half-life so as not to emit a significant amount of beta or gamma radiation are listed in Table I without an asterisk; those marked with an asterisk in Table I may form small amounts of unwanted radioactive isotopes.

In accordance with the present invention, the constituent elements of the glass may be chosen so that the radiation may be tailored to deliver a radiation profile that is ideally suited for a particular treatment. For instance, in some instances it may be preferred to employ a radiotherapeutic product with short-lived beta emitter Y-90, while in others it may be preferred to utilize the longer-lived beta emitter P-32 or a product that has both components. In other instances, it may be desirable to employ a radiotherapeutic product with a gamma emitting isotope or a mixture of beta and gamma emitting isotopes. The microspheres of the present invention permit this versatility: a combination of elements having the desired radiation emission profile may be incorporated into the glass material. In a preferred embodiment, a beta emitter and/or a low energy gamma emitting nuclide is incorporated into the microspheres. In a most preferred embodiment, yttrium and/or phosphorus are incorporated into the microspheres; P-32 emits pure beta radiation and Y-90 emits nearly pure beta radiation which will spare healthy tissue remote from the tumor site in which the microsphere is embedded.

The constituent elements of the microspheres of the present invention are also preferably chosen so that the microsphere does not contain any significant amount of elements which have a large cross-section for neutrons. An example of one such element that has a large cross-section for neutrons is boron which has a cross-section of 3837 barns. In a most preferred embodiment, the microspheres do not contain a significant amount of any elements that have a cross-section for neutrons greater than about 200 barns.

The radiation dosage delivered through the use of the activated microspheres upon administration to the patient can be varied by controlling the number of microspheres administered and by controlling the amount of radiation emitting isotopes contained by the microspheres. The amount of radiation emitting isotopes contained by the microspheres is affected by two factors: the amount of the stable element that will be converted to a radioelement by irradiation, and the length of time of irradiation. Preferably, the microspheres are irradiated for a short period of time with an intense thermal neutron flux generated by a nuclear fission reactor instead of being irradiated for a significantly longer period of time with a lesser neutron flux. This technique of a short, intense irradiation of the microsphere is particularly preferred where one or more of the constituent elements of the microsphere has an undesired radiation profile and a half-life that is significantly greater than those constituent elements having a desired radiation profile. Thus, the manner of irradiation may be controlled in such a manner to impart the microsphere with a therapeutic intensity and amount of radiation while also minimizing the amount of undesired radiation.

The microspheres of the present invention may be processed to have a size that is appropriate for the therapeutic application. The characteristics of the tissue in which the microspheres will be embedded generally dictate the appropriate size of the microspheres to be employed. Generally, microspheres having a size somewhere within the range of about 5 to about 75 micrometers are employed for therapeutic applications and in many cases it is preferred that the microspheres have a size somewhere within the range of about 5 to about 50 micrometers. For instance, in the treatment of liver cancer, it is preferred to employ microspheres having a size substantially within the range of about 20 to about 30 micrometers; microspheres of this size are small enough to be conveniently delivered to the liver through the hepatic artery but are too large to pass through the capillary bed of the liver.

The microspheres may be administered to the patient through the use of catheters either alone or in combination with vasoconstricting agents or by any other means of administration that effectively causes the microspheres to become embedded in the cancerous or tumor bearing tissue. For purposes of administration, the microspheres are preferably suspended in a medium that has a sufficient density or viscosity that prevents the microspheres from settling out of suspension during the administration procedure. Presently preferred liquid vehicles for suspension of the microspheres include polyvinylpyrrolidone (PVP), sold under the trade designation Plasdone K-30 and Povidone by GAF Corp, a contrast media sold under the trade designation Metrizamide by Nyegard & Co. of Oslo, Norway, a contrast media sold under the trade designation Renografin 76 by E. R. Squibb & Co., 50% dextrose solutions and saline.

The microspheres of the present invention may be prepared from a homogenous mixture of powders (i.e., the batch) that is melted to form the desired glass composition. The exact chemical compounds or raw materials used for the batch is not critical so long as they provide the necessary oxides in the correct proportion for the melt composition being prepared. For instance, if a YAS glass is being made, then yttria, alumina, and silica powders could be used as the batch raw materials. The purity of each raw material is preferably greater than 99.9%. After either dry or wet mixing of the powders to achieve a homogeneous mixture, the mixture may be placed in a platinum crucible for melting. High purity alumina crucibles can also be used if at least small amounts of alumina can be tolerated in the glass being made. The crucibles containing the powdered batch are then placed in an electric furnace which is heated 1500° to 1600° C., depending upon the composition. In this temperature range, the batch melts to form a liquid which is stirred several times to improve its chemical homogeneity. The melt should remain at 1500° to 1600° C. till all solid material in the batch is totally dissolved, usually 2-5 hours being sufficient. When melting and stirring is complete, the crucible is removed from the furnace and the melt is quickly quenched to a glass by pouring the melt onto a cold steel plate or into clean water. This procedure breaks the glass into fragments, which aids and simplifies crushing the glass to a fine powder. The powder is then sized and spheroidized for use.

Where it is desired to use microspheres having a diameter in the range of about 20 to about 30 micrometers as for example in the treatment of liver cancer, it is preferred that the quenched and broken glass be first crushed to about minus 100 mesh particles using a mortar and pestle. The minus 100 mesh material is then ground using a mechanized mortar and pestle or ball mill, until it passes a 400 mesh sieve. The particles are formed into glass microspheres by introducing the −400 mesh particles into a gas/oxygen flame where they are melted and a spherical liquid droplet is formed by surface tension. The droplets are rapidly cooled before they touch any solid object so that, their spherical shape is retained in the solid product.

Just prior to spheroidizing, the −400 mesh powder is rescreened through a 400 mesh sieve to destroy any large agglomerates that may have formed during storage. The −400 mesh powder is then placed in a vibratory feeder located above the gas/oxygen burner. The powder is slowly vibrated into a vertical glass tube which guides the falling powder particles directly into the hot flame of a gas/oxygen burner. Any burner capable of melting −400 mesh particles of the particular glass composition being used is satisfactory. A typical rate for feeding the powder to the flame is 5 to 25 gm/hr with the described apparatus. The flame of the burner is directed into a metal container which catches the small glass beads as they are expelled from the flame. This container can be made of any metal which can withstand the heat of the burner and does not contaminate the glass. The container needs to be large enough so that the molten spheres can cool and become rigid before hitting any solid surface of the catcher container.

After spheroidization, the glass spheres are collected and rescreened. When the microspheres are intended to be used in the treatment of liver cancer, the fraction less than 30 and greater than 20 micrometers in diameter is recovered since this is the desirable size for use in the human liver. After screening, the −30/+20 microspheres are examined with an optical microscope and are then washed with a weak acid (HCl, for example), filtered, and washed several times with reagent grade acetone. The washed spheres are then heated in a furnace in air to 500°-600° C. for 2-6 hours to destroy any organic material.

The final step is to examine a representative sample of the −30/+20 spheres in a scanning electron microscope to evaluate the size range and shape of the spheres. The quantity of undersize spheres (less than 10 micrometers in diameter) is determined along with the concentration of non-spherical particles. The composition of the spheres can be checked by energy dispersive x-ray analysis to confirm that the composition is correct and that there is an absence of chemical contamination.

The glass microspheres are then ready for irradiation and subsequent administration to the patient.

In accordance with the present invention, the above processing steps are merely exemplary and do not in any way limit the present invention. For instance, those skilled in the art will appreciate the steps involved in producing a microshell or a microsphere having a plurality of hollow cells. Similarly, the present invention is not limited to glass microspheres having a size described above; the size of the microspheres of the present invention may be varied according to the application.

In accordance with a preferred embodiment, the microspheres of the present invention may be advantageously used in the treatment of liver cancer. For this purpose, it is presently preferred to use essentially void-free YAS glass microspheres having a composition lying within the previously identified quadrilateral region of the yttria alumina-silica composition diagram and that have an activity of about 0.2 to about 0.6 Ci/gm of glass after irradiation. To achieve the desired level of activity, the YAS microspheres are irradiated for an effective period. For instance, YAS microspheres comprising about 40% by weight yttria are irradiated in a nuclear reactor to a level of about 3 Ci/gm which requires about 75 hours of irradiation at $1 \times 10^{14}$ neutrons/cm$^2$sec. Thus, by activating the microspheres to a level above the preferred administration range, decay of activity of the activated microspheres may occur during processing and shipment prior to administration to the patient and still permit administration within the preferred range of activity. If microshells or microspheres comprising a plurality of hollow cells are used instead of solid microspheres, the specific activity after irradiation needs to be higher in order to account for the decrease in mass of similarly sized spheres. If it were preferred to use a glass microsphere containing P-32 instead of Y-90 for the treatment of liver cancer, the specific activity required through irradiation may be considerably lower than that required for Y-90 microspheres; P-32 has a longer half-life than Y-90 (14.3 days vs. 64 hours for Y-90) which results in less decay during transit and which causes it to remain active in the body longer than Y-90.

The microspheres of the present invention may be used in the treatment of liver cancer by introducing a catheter into the hepatic artery and administering the radioactive microspheres. Preferably, the microspheres are suspended in a medium such as Plasdone K-30 or Metrizamide for purposes of administration. The particle density in the liver after administration is preferably on the order of about 4000 microspheres per gram of liver. When administered in this manner, the microspheres become embedded in the capillary bed of the tumorous liver tissue rather than in normal liver, thereby delivering the radiation dosage primarily to the tumor. Vasoconstricting drugs may additionally be used to decrease hepatic artery flow to normal liver. Microspheres used in this treatment preferably comprise either P-32 or Y-90 because of their short-ranged radiation.

Other cancerous or tumor bearing tissue may similarly be treated with the microspheres of the present invention. Depending upon the application, it may be desirable to incorporate a gamma emitting radioisotope or a combination of gamma and beta emitting radioisotopes into the microsphere. Alternatively, a physical mixture of microspheres having different radiation profiles may be used in order to tailor the treatment for a particular case. For instance, the treatment may comprise administration of a physical mixture of two different microspheres, the first type containing Y-90 and the second type containing P-32.

The following examples illustrate the invention.

EXAMPLE 1

A. MICROSPHERE PREPARATION

The glass compositions listed in Table II were prepared from reagent grade chemicals. Batches yielding 50 grams of glass were melted in platinum crucibles in an electric furnace at the approximate temperatures in Table II. A typical melting cycle required three hours for batch additions at 1000° C. and three to four hours to refine the melt at the approximate melting temperature. The crucible containing the melt was quenched in 25° C. water, after which the resultant glass frit was broken from the crucible and ground to −100 mesh. The −100 mesh glass powder was then slowly fed by a vibrating spatula into an oxygen/propane flame where surface tension pulled the molten particles into spheres. The flow rates of oxygen and propane were adjusted for each glass composition so as to yield the highest fraction of spherical particles. After spheroidizing, the microspheres were wet screened with deionized water, rinsed in acetone and dried.

B. CHEMICAL DURABILITY MEASUREMENTS

The compositions marked with an asterisk in Table II were immersed in deionized water at 50° C. and the release of elemental phosphorus measured as a function of time. Samples of 76 to 150 μm diameter microspheres, each sample weighing 0.5 gm, were placed in high density polyethylene bottles with 25 ml of deionized water. The bottles were then placed in an oven at 50° C.±5° C. for 7, 15, 30, and 40 days with brisk agitation for 5 seconds on days 2 and 27. After removing a sample from the oven, the aqueous phase was filtered through Whatman #52 filter paper. Each filtrate was then fumed with Perchloric acid (70–72%) at 75° C. to remove any soluble silica that might interfere with the spectrophotometric determination of phosphorus. In the determination of phosphorus, the fumed solutions were mixed with an acidic ammonium vanadate, ammonium molybdate reagent to form a yellow vanadomolybdate-phosphoric acid complexes. The concentration of phosphorus was calculated from the absorbence of the solution measured at 400 nm.

C. SPECTROPHOTOMETRIC DETERMINATION OF PHOSPHORUS

Samples of 25 ml deionized water in which 0.5 gm of microspheres had been immersed at 50° C. for 7, 15, 30, and 40 days were prepared for determination of phosphorus content. Standardized solutions of known phosphorus ppm were prepared and their absorbence measurements at 400 nm. plotted. From this standardization curve, the measured absorbence values at 400 nm. from the sample specimens were converted to ppm phosphorus concentrations. These values were then multiplied by dilution factors and converted to the weight of phosphorus confirmed in the sample specimens, shown in Table V. Division by the weight of phosphorus in the known initial weight of glass yields the wt % of phosphorus leached given in Table V.

The calibration curve becomes non-linear at very low concentrations. This uncertainty in using the calibration line to calculate the phosphorus ppm in solution increases with decreasing phosphorus concentration. One ppm standard solutions are 4% in error by the time absorbence measurements are converted back to ppm values from the calibration curve. This error reaches 6% for 0.5 ppm phosphorus standard solutions. Testing standards of 0.1 ppm phosphorus and converting absorbence values back to ppm values by the calibration curve yields errors up to 22%. Since all solutions tested had calculated concentrations of phosphorus greater than 0.168 ppm, it is safe to assume the maximum error in the wt % phosphorus leached values to be less than 22%. The error in values decreases as the concentration of phosphorus in the test specimen increases.

D. COMPOSITIONAL OVERVIEW

The glass compositions evaluated in this example can be generally classified as either a modified soda-lime silica or a magnesium aluminosilicate. In the soda-lime compositions, the lime was eliminated so as to preclude the formation of unwanted $^{45}Ca$, and replaced with magnesium and/or potassium. Alumina was added to nearly all the compositions (see Table II), to improve the chemical durability. Compositions UMR-17 and UMR-25 contain zirconia, which significantly improves the resistance of other silicate glasses to alkaline attack. Manganese dioxide was added to UMR-24 also to improve the resistance to alkaline attack.

In attempts to reduce the melting temperatures and viscosity, and to keep the alkali content low, lead oxide was included in a number of batches, and the magnesium carbonate in the batch was replaced by magnesium fluoride. The fluxing ability of the lead oxide additions appeared minimal at levels less than 10 wt %. Higher additions caused phase separation. The substitution of magnesium fluoride for magnesium carbonate during batching showed a slight improvement in lowering the melt viscosity.

E. SPHEROIDIZATION

In composition UMR-24 large bubbles developed in some of the microspheres during spheroidization. During subsequent wet screening, the hollow microspheres could easily be separated from the solid spheres by floating the hollow spheres away from the heavier solid spheres. The formation of bubbles in glass microspheres is of interest as a means of lowering the bulk density of the microspheres. Table III lists the density of currently used essentially void-free microspheres, and the measured values for the seven glass compositions evaluated in the chemical durability tests. The higher density of glass microspheres requires a suspending solution with either a higher viscosity or higher density to prevent settling of the microspheres prior to their use.

F. STRAY RADIATION TESTING

The compositions evaluated for chemical durability were also studied after neutron irradiation to check for the emission of undesired radiation and a low, tolerable background of undesirable radiation was found in almost all compositions. Only UMR-17 contained a significant amount of an unwanted radioactive isotope and may not be considered acceptable for use in the treatment of liver cancer. The unwanted radioactive isotope, $^{95}Zr$, formed from the 12 wt % zirconia in the glass. By reducing the zirconia to 4 wt %, the unwanted radiation was lowered to such a level that UMR-26 is acceptable for this application based on this evaluation.

G. CHEMICAL DURABILITY TESTING

Figure 2:
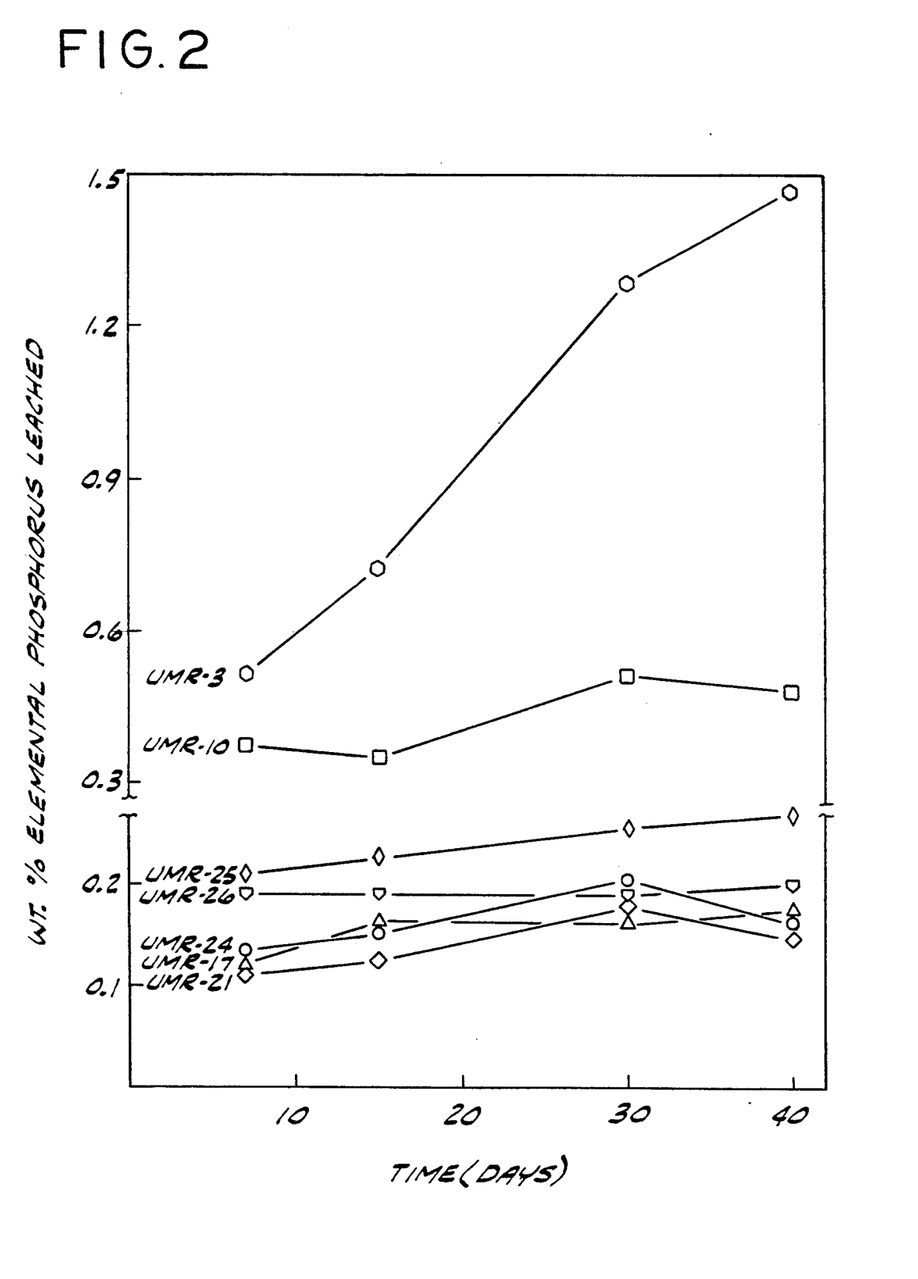
FIG. 2 is a series of plots showing the weight proportion of elemental phosphorus leached from various microspheres of the invention as a function of time of exposure to deionized water at 50° C.

Results from the elemental phosphorus leaching test are shown in FIG. 2. The wt % phosphorus leached was calculated from the weight of phosphorus found in solution, divided by the initial weight of phosphorus in the microspheres. The decrease in phosphorus release between glasses UMR-3 and UMR-10 is attributed to changing the alkali from sodium to potassium, and to the reduction in the total alkali content of the glass with a corresponding increase in the silica content. The remaining compositions are closely grouped with the high zirconia containing glass, UMR-17, and the magnesium alumino silicate, UMR-21, showing the lowest phosphorus releases.

Any chemical corrosion of the glass microspheres by deionized water is expected to change the solution pH. To a limited extent the change in pH should be proportional to the degree of chemical reaction. The PH values of the solution after 74 days at 50° C. is given in Table IV. The higher pH values indicate UMR-3 and UMR-25 have significantly reacted with the water relative to the other compositions.

Figure 3:
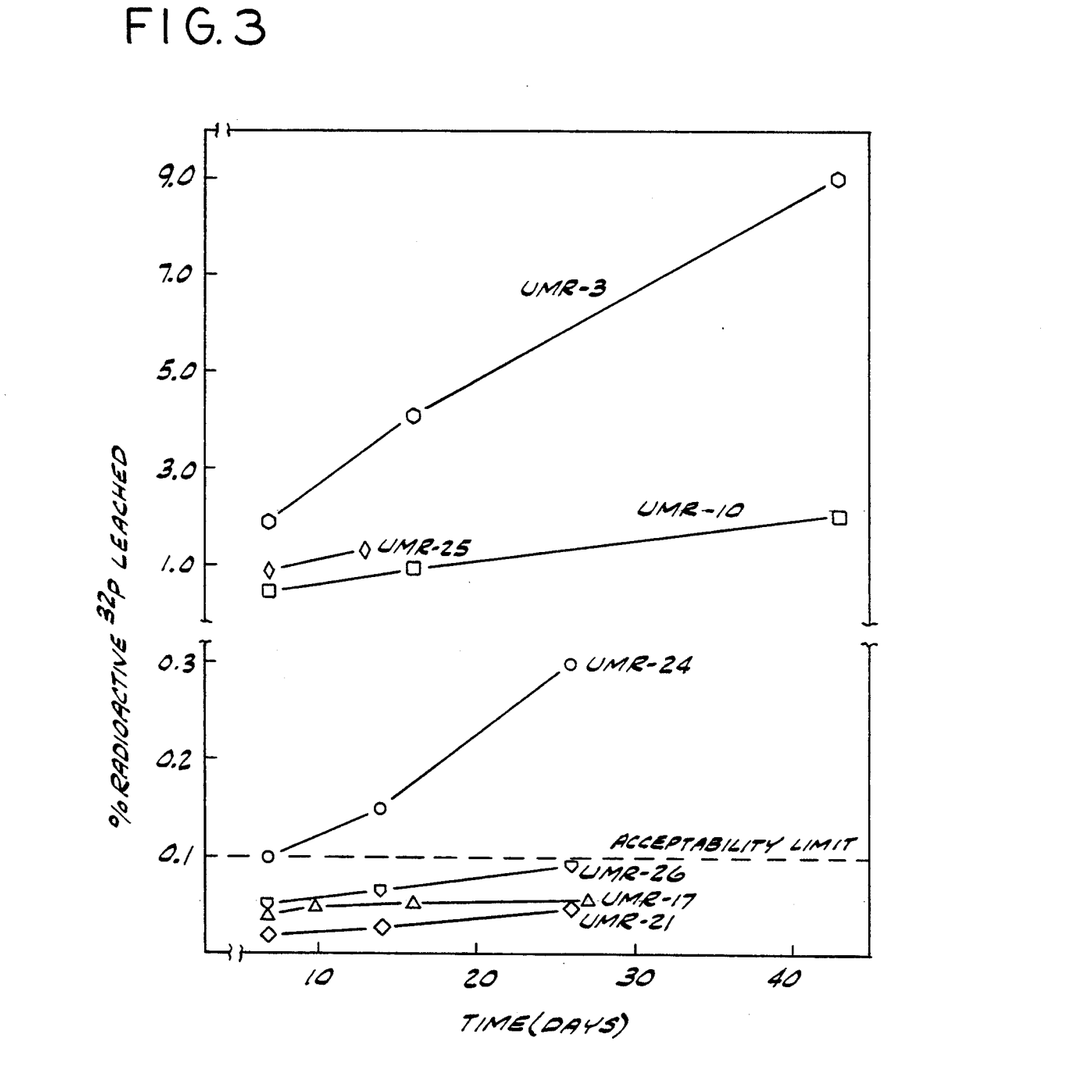
FIG. 3 is a plot similar to FIG. 2 showing leaching of radioactive phosphorus from microspheres exposed to human blood plasma at 37° C.

In the second durability test, the release of radioactive $^{32}P$ was measured for the same glasses used in the first durability test. In this test, microspheres 46 to 75 μm in diameter were first rinsed in 0.12 N HCl at room temperature, rinsed in deionized water and then neutron irradiated. After irradiation, the microspheres were again rinsed in 0.12 N HCl, rinsed in deionized water and transferred to vials containing 10 ml of human blood plasma at 37° C. Samples of human blood plasma (1.1 ml), were removed from the vials periodically and their beta radioactivity measured with a liquid scintillation counter. The activity of subsequent samples was corrected for the decreasing volume of plasma in the vial. In FIG. 3, the percent radioactive phosphorus leached is the radioactivity of phosphorus in solution divided by the decaying total of radioactive phosphorus in the glass.

Comparison of the phosphorus leaching data in FIGS. 1 and 2 show a good correlation in the relative ranking of glasses evaluated. The combined information gathered in the first durability test and pH testing is representative of how compositions performed in the second test, thus these methods can be used to accurately screen future compositions without handling radioactive samples.

To determine the suitability of glasses based on their release of radioactive phosphorus, a maximum value of 0.1% radioactive phosphorus leached after 30 days was arbitrarily established. This value represents the estimated maximum extent of leaching from a 5% by weight phosphorus pentoxide glass which will produce radioactive P-32 level below the maximum level which a healthy adult can tolerate in his body without adverse effect.

In FIG. 3, three compositions satisfy the adopted value of 0.1% radioactive phosphorus leached after 30 days; they are UMR-21, UMR-17, and UMR-26. As previously noted, UMR-17 has undesirable radioactive emissions that make it unacceptable for this application. UMR-21 is a magnesium alumina silicate composition which had the lowest release of phosphorus in both leaching tests.

TABLE III

DENSITY OF TYPICAL MICROSPHERE MATERIALS AND SELECTED GLASS SAMPLES

| Material | Sample | Density (g/cm³) |
|---|---|---|
| Plastic | (Polystyrene) | 1.05 |
| Ceramic* | (bulk density) | 2.00 |
| Glass | | |
| | UMR-3 | 2.41 |
| | UMR-10 | 2.35 |
| | UMR-17 | 2.56 |
| | UMR-21 | 2.55 |
| | UMR-24 | 2.37 |
| | UMR-25 | 2.38 |

TABLE III-continued

DENSITY OF TYPICAL MICROSPHERE MATERIALS AND SELECTED GLASS SAMPLES

| Material | Sample | Density (g/cm³) |
|---|---|---|
| | UMR-26 | 2.37 |

*3M Co., St. Paul, MN

TABLE IV

PH OF DEIONIZED WATER IN CONTACT WITH GLASS MICROSPHERES AFTER 74 DAYS AT 50° C.

| Sample | pH |
|---|---|
| Water Blank | 4.70 |
| UMR-17 | 7.30 |
| UMR-10 | 7.30 (7.40)* |
| UMR-21 | 7.30 (7.60)* |
| UMR-26 | 7.45 |
| UMR-24 | 7.90 (8.00)* |
| UMR-25 | 8.95 (8.95)* |
| UMR-3 | 9.50 (9.50)* |

*Duplicate sample

EXAMPLE 2

The glass compositions listed in Table VI were prepared from reagent grade materials. Batches of 25 or 50 grams were melted in platinum crucibles in an electric furnace at 1500° to 1600° C. A period of 2 to 3 hours at temperature was allowed for fining and homogenization of the melt. The glasses were cast into bars measuring approximately 1×1×6 cm in steel molds and were annealed at approximately 800° C. for 8 to 12 hours. Excess glass in the crucibles was quenched in water, broken from the crucible, and saved for spheroidizing. Spheroidization of each of the glasses into microspheres was performed according to the procedures of Example 1. Table VI also lists the density, pouring temperature and appearance for each of the glasses identified.

The glass compositions listed in Table VI were also evaluated for chemical durability with the results being provided in Table VII. Table VII provides the dissolution rate for YAS glass samples 2-8 and for vitreous silica as determined in 1N HCl under the conditions specified.

Figure 4:
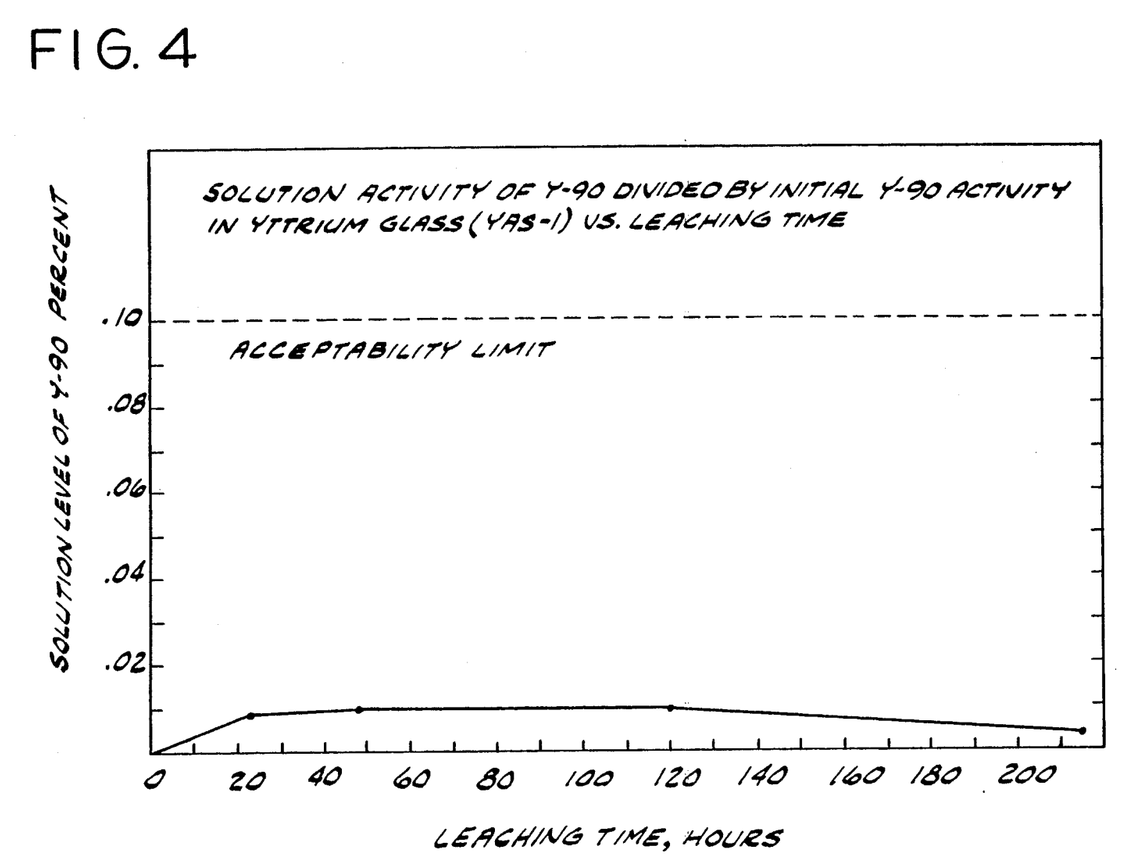
FIG. 4 is a plot of solution activity of Y-90 divided by initial Y-90 activity versus time for a YAS glass sample evaluated in Example 2.

FIG. 4 reports the percent radioactive yttrium leached from sample YAS-1 over time and under the conditions expressed in Table VII. Each point in FIG. 4 represents the amount of radiation measured in solution divided by the initial Y-90 activity, the ratio being expressed as a percent. When expressed in this manner, it is apparent that the amount of Y-90 leached from the microsphere is well within the acceptability limit.

Figure 5:
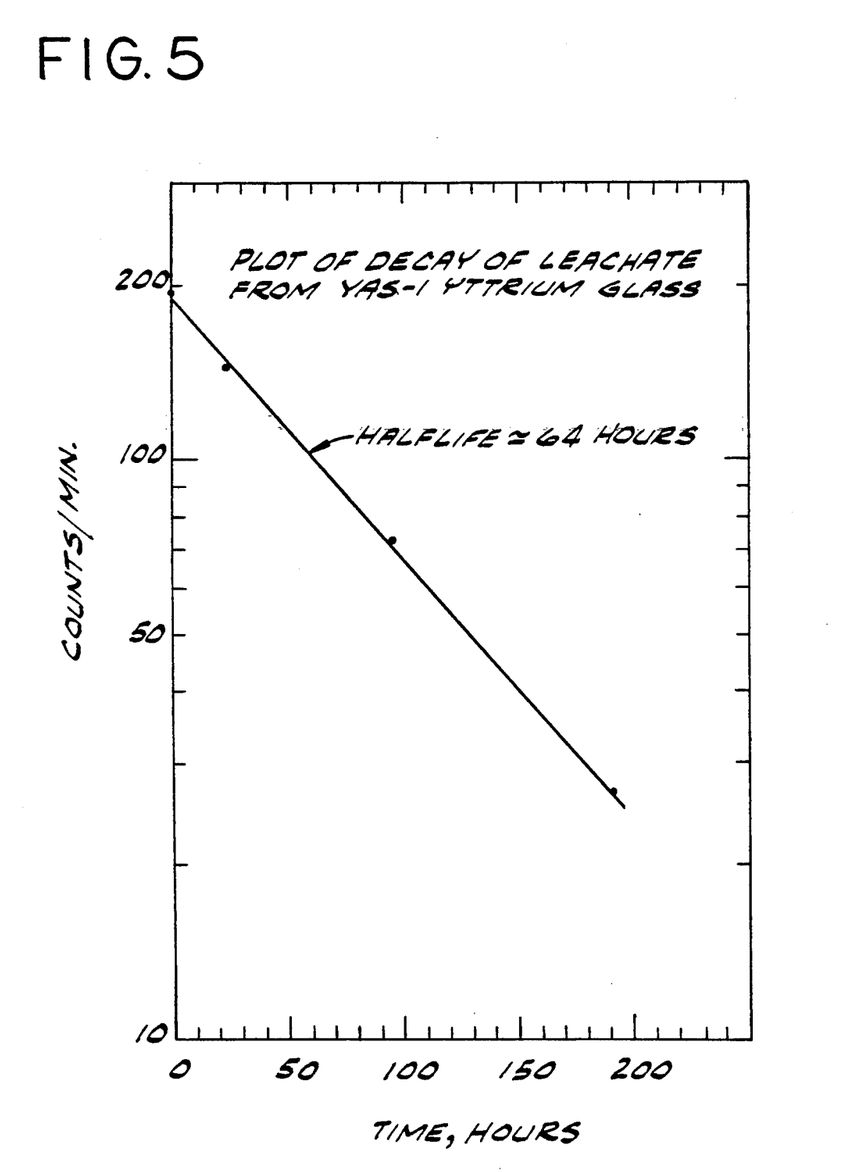
FIG. 5 is a plot of decay of leachate from a YAS glass sample versus time containing the results of Example 2.

In FIG. 5, each point represents the measured activity of leachate from sample YAS-1 over time and under the conditions expressed in Table VII. Also presented on this plot is a line representing the half-life of Y-90. The high degree of correlation between the points and this line demonstrate that there was not a significant amount of any radioisotope other than Y-90 leached from sample YAS-1.

TABLE VI

| Sample | Composition (wt %) | | | Density Gm/cm³ | Pouring Temp, °C. | Appearance |
|---|---|---|---|---|---|---|
| YAS-1 | 33 | 21 | 46 | 3.07 | 1500 | Viscous, Clear Glass |
| YAS-2 | 55 | 20 | 55 | 3.81 | 1550 | Fluid |
| YAS-3 | 50 | 20 | 30 | 3.65 | 1550 | Fluid, Clear Glass |

TABLE VI-continued

| Sample | Composition (wt %) | | | Density Gm/cm³ | Pouring Temp, °C. | Appearance |
|---|---|---|---|---|---|---|
| YAS-4 | 40 | 20 | 40 | 3.29 | 1500 | Fluid, Clear Glass |
| YAS-5 | 25 | 20 | 55 | 2.84 | 1600 | Viscous, Opal Glass |
| YAS-6 | 42 | 25 | 33 | 3.42 | 1500 | Fluid, Clear Glass |
| YAS-7 | 40 | 30 | 30 | 3.39 | 1500 | Fluid, Clear Glass |
| YAS-8 | 40 | 13 | 47 | 3.23 | 1600 | Fluid, Opal Glass |
| YAS-9 | 55 | 15 | 30 | 3.81 | 1600 | Fluid, Clear Glass |
| YAS-10 | 35 | 35 | 30 | 3.30 | 1600 | Fluid, Clear Glass |

TABLE VII

DISSOLUTION RATES IN 1N HCl OF YAS GLASSES AND VITREOUS SILICA

| Glass | Dissolution Rate (g/cm²min) | | |
|---|---|---|---|
| | 6 days @ 50° C. | 15 days @ 30° C. | 7 days @ 50° C. |
| YAS-2 | $54.6 \times 10^{-7}$ | | |
| 3 | $36.2 \times 10^{-7}$ | | |
| 4 | $7.8 \times 10^{-7}$ | $2.8 \times 10^{-7}$ | $2.1 \times 10^{-7}$ |
| 5 | $3.4 \times 10^{-7}$ | | |
| 6 | $28.1 \times 10^{-7}$ | | |
| 7 | $28.3 \times 10^{-7}$ | $5.7 \times 10^{-7}$ | $6.8 \times 10^{-7}$ |
| 8 | $7.2 \times 10^{-7}$ | $3.9 \times 10^{-7}$ | $2.8 \times 10^{-7}$ |
| SiO₂ | | $5.0 \times 10^{-8}$ | $5.5 \times 10^{-9}$ |

In view of the above, it will be seen that the several objects of the invention are achieved and other advantageous results attained.

As various changes could be made in the above methods and products, without departing from the scope of the invention, it is intended that all matter contained in the above description or shown in the accompanying drawings shall be interpreted as illustrative and not in a limiting sense.

What is claimed is:

1. A radioactive microsphere for radiation therapy of a mammal comprising a biologically compatible glass material containing at least one beta or gamma radiation emitting isotope distributed substantially throughout the glass which emits a therapeutic intensity and amount of beta or gamma radiation, and a balance of elements selected from the group consisting of elements that do not become radioactive upon neutron irradiation and elements that have a half-like that is sufficiently short so that the elements do not emit a significant amount of beta or gamma radiation at the time of administration, the microsphere having a chemical durability such that subsequent to administration of the microsphere to the mammal, the microsphere will not release a significant amount of the radiation emitting radioisotope into the mammal's system.

2. A radioactive microsphere as set forth in claim 1 wherein said glass comprises an aluminosilicate glass.

3. A radioactive microsphere as set forth in claim 1 wherein said glass comprises an yttrium oxide-aluminosilicate glass.

4. A radioactive microsphere as set forth in claim 1 wherein said glass comprises a lead silicate glass.

5. A radioactive microsphere as set forth in claim 1 wherein said glass comprises an yttrium oxide-aluminosilicate glass having a composition lying substantially within a quadrilateral region of the ternary composition diagram of the yttria-alumina-silica system, the quadrilateral region being defined by its four corners having the following combination of weight Proportions of the components: 20% silica, 10% alumina, 70% yttria; 70% silica, 10% alumina, 20% yttria; 70% silica, 20% alumina, 10% yttria; and 20% silica, 45% alumina, 35% yttria.

6. A radioactive microsphere as set forth in claim 1 wherein said radioisotope comprises phosphorus-32.

7. A radioactive microsphere as set forth in claim 1 wherein said microsphere is selected from the group consisting of essentially void-free microspheres, microspheres having a hollow core and microspheres having a plurality of hollow cells.

8. A radioactive microsphere as set forth in claim 1 wherein said radioisotope having been formed by neutron irradiation of the microsphere.

9. A radioactive microsphere as set forth in claim 1 wherein said glass material is substantially free of elements having a cross-section for neutrons greater than about 200 barns.

10. A radioactive microsphere as set forth in claim 1 wherein said at least one beta or gamma radiation emitting isotope is selected from the group consisting of isotopes having a half-like greater than about 2 and less than about 30 days.

11. A radioactive microsphere as set forth in claim 1 wherein the beta or gamma radiation emitting isotope is phosphorous-32.

12. A radioactive microsphere as set forth in claim 1 wherein the balance of elements are selected from the group of elements consisting of carbon, nitrogen, oxygen, fluorine, sodium, magnesium, aluminum, silicon, potassium, vanadium, manganese, gallium, niobium, iodine and lead.

13. A radioactive microsphere as set forth in claim 1 wherein said glass contains between about 50 and about 70 wt. % silica, between about 1 and about 17 wt. % alumina; between about 5 and about 9 wt. % magnesia; and between about 2 and about 10 wt. % phosphorus pentoxide.

14. A radioactive microsphere as set forth in claim 13 wherein said glass comprises a magnesium aluminosilicate glass.

15. A radioactive microsphere as set forth in claim 13 wherein said glass further comprises between about 7 and about 15 wt. % $K_2O$.

16. A radioactive microsphere as set forth in claim 15 wherein said glass further comprises between about 2 and about 6 wt. % zirconia.

17. A radioactive microsphere as set forth in claim 1 wherein said radioisotope comprises yttrium-90.

18. A radioactive microsphere as set forth in claim 17 wherein said microsphere has a radiation density of about 2 Ci/gm.

19. A radioactive microsphere as set forth in claim 1 wherein said microsphere is substantially spherical in shape and has a diameter in the range of about 5 to about 75 micrometers.

20. A radioactive microsphere as set forth in claim 19 wherein the beta or gamma radiation emitting radioisotope comprises a radioisotope selected from the group consisting of yttrium-90 and phosphorous-32.

21. A radioactive microsphere as set forth in claim 1 wherein the balance of elements are selected from the group of elements consisting of carbon, nitrogen, oxygen, fluorine, sodium, magnesium, aluminum, silicon, potassium, vanadium, manganese, gallium, niobium, iodine, lead, titanium, copper, germanium, and zirconium.

22. A radioactive microsphere as set forth in claim 21 wherein the beta or gamma radiation emitting isotope is phosphorous-32.

23. A radioactive microsphere adapted for radiation therapy of a mammal comprising a glass having phosphorous-32 or yttrium-90 distributed substantially through the glass, the microsphere having a chemical durability such that subsequent to administration of the microsphere to the mammal, the microsphere will not release a significant amount of the radiation emitting radioisotope into the mammal's system.

24. A radioactive microsphere as set forth in claim 23 wherein said microsphere is selected from the group consisting of essentially void-free microspheres, microspheres having a hollow core and microspheres having a plurality of hollow cells.

25. A radioactive microsphere as set forth in claim 23 wherein said glass comprises an aluminosilicate glass, an yttrium oxide-aluminosilicate glass, or a lead silicate glass.

26. A radioactive microsphere as set forth in claim 23 wherein the microsphere has a diameter between about 5 and about 75 micrometers.

27. A radioactive microsphere as set forth in claim 23 wherein the microsphere has a diameter between about 20 and about 30 micrometers.

28. A radioactive microsphere as set forth in claim 23 wherein the microsphere has a hollow core or a plurality of hollow cells.

29. A radioactive microsphere as set forth in claim 23 wherein the microsphere comprises phosphorus-32.

30. A radioactive microsphere as set forth in claim 23 wherein said glass further comprises between about 50 and 70 wt. % silica, between about 1 and about 17 wt. % alumina, between about 5 and about 9 wt. % magnesia, between about 2 and about 10 wt. % phosphorous pentoxide, and between about 7 and about 15 wt. % $K_2O$.

31. A radioactive microsphere as set forth in claim 30 wherein said glass further comprises between about 2 and about 6 wt. % zirconia.

32. A radioactive microsphere as set forth in claim 23 wherein the microsphere has a diameter between about 5 and about 75 micrometers, and contains phosphorous-32 or yttrium-90 and a balance of elements selected from the group consisting of elements that do not become radioactive upon neutron irradiation and elements that have a half-life that is sufficiently short so that the elements do not emit a significant amount of beta or gamma radiation at the time of administration.

33. A radioactive microsphere as set forth in claim 32 wherein the balance of elements are selected from the group of elements consisting of carbon, nitrogen, oxygen, fluorine, sodium, magnesium, aluminum, silicon, potassium, vanadium, manganese, gallium, niobium, iodine and lead.

34. A radioactive microsphere as set forth in claim 32 wherein the balance of elements are selected from the group of elements consisting of carbon, nitrogen, oxygen, fluorine, sodium, magnesium, aluminum, silicon, potassium, vanadium, manganese, gallium, niobium, iodine, lead, titanium, copper, germanium, and zirconium.

35. A radioactive microsphere as set forth in claim 32 wherein the microsphere has a hollow core or a plurality of hollow cells.

36. A method of radiation therapy of a mammal comprising administering to said mammal microspheres comprising a glass material containing a beta or gamma radiation emitting isotope distributed substantially uniformly throughout the glass, the microsphere having a chemical durability such that subsequent to administration of the microspheres to the mammal, the microspheres will not release a significant amount of the radiation emitting radioisotope into the mammal's system.

37. A method as set forth in claim 36 wherein prior to administration the radioisotope has been formed by irradiation of the microsphere.

38. A method of radiation therapy of a mammal comprising embedding in the capillary bed of the mammal's liver microspheres comprising a glass material containing a beta or gamma radiation emitting isotope distributed substantially uniformly throughout the glass, the microspheres having sufficient chemical durability so as to avoid the release of a significant amount of radiation emitting isotope into the mammal's system.

39. A method as set forth in claim 38 wherein said isotope is yttrium-90.

40. A method as set forth in claim 38 wherein said isotope is phosphorous-32.

41. A method as set forth in claim 38 wherein said microsphere has a diameter less than about 75 micrometers.

42. A radioactive glass microsphere adapted for radiation therapy of a mammal, the glass microsphere comprising an yttrium oxide-aluminosilicate glass containing yttrium-90 and having a composition lying substantially within a quadrilateral region of the ternary composition diagram of the yttria-alumina-silica system, the quadrilateral region being defined by its four corners having the following combination of weight proportions of the components: 20% silica, 10% alumina, 70% yttria; 70% silica, 10% alumina, 20% yttria; 70% silica, 20% alumina, 10% yttria, and 20% silica, 45% alumina, 35% yttria.

43. A radioactive glass microsphere adapted for radiation therapy of a mammal having phosphorous-32 distributed substantially throughout the glass, the glass additionally containing between about 50 and 70 wt. % silica, between about 1 and about 17 wt. % alumina, between about 5 and about 9 wt. % magnesia, and between about 2 and about 10 wt. % phosphorous pentoxide.

44. A radioactive glass microsphere adapted for radiation therapy of a mammal comprising, phosphorous-32 or yttrium-90 distributed substantially throughout the glass and a balance of elements selected from the group of elements consisting of carbon, nitrogen, oxygen, fluorine, sodium, magnesium, aluminum, silicon, potassium, vanadium, manganese, gallium, niobium, iodine, lead, titanium, copper, germanium, and zirconium, the microsphere having a size between about 5 and about 75 micrometers and having a chemical durability such that subsequent to administration of the microsphere to the mammal, the microsphere will not release a significant amount of the radiation emitting radioisotope into the mammal's system.

45. A biologically compatible radioactive glass microsphere for radiation therapy of a mammal comprising at least one beta or gamma radiation emitting isotope having a half-like greater than about 2 and less than about 30 days distributed substantially throughout the glass which emits a therapeutic intensity and amount of beta or gamma radiation, and a balance of elements selected from the group consisting of elements that do not become radioactive upon neutron irradiation and elements that have a half-like that is sufficiently short so that the elements do not emit a significant amount of beta or gamma radiation at the time of administration, the microsphere having a chemical durability such that subsequent to administration of the microsphere to the mammal, the microsphere will not release a significant amount of the radiation emitting radioisotope into the mammal's system.

* * * * *

UNITED STATES PATENT AND TRADEMARK OFFICE
CERTIFICATE OF CORRECTION

PATENT NO. : 5,011,677

DATED : April 30, 1991

INVENTOR(S) : Delbert E. Day et al.

It is certified that error appears in the above—identified patent and that said Letters Patent is hereby corrected as shown below:

Column 14, claim 5, line 66, "Proportions", should read ---proportions---.

Column 15, claim 18, line 50, "2Ci/gm", should read ---3Ci/gm---.

Column 16, claim 23, line 4, "through the glass", should read ---throughout the glass---.

Signed and Sealed this

Fifteenth Day of September, 1992

Attest:

DOUGLAS B. COMER

Attesting Officer

Acting Commissioner of Patents and Trademarks